United States Patent [19]

Aoki et al.

[11] Patent Number: 5,047,503

[45] **Date of Patent: * Sep. 10, 1991**

[54] THROMBIN-BINDING SUBSTANCE AND PROCESS FOR ITS PREPARATION

[75] Inventors: Nobuo Aoki, Tokyo; Shigeru Kimura, Higashiyamato; Masami Shiratsuchi, Musashimurayama, all of Japan

[73] Assignee: Kowa Company, Ltd., Nagoya, Japan

[ * ] Notice: The portion of the term of this patent subsequent to May 3, 2007 has been disclaimed.

[21] Appl. No.: 72,051

[22] Filed: Jul. 10, 1987

[30] Foreign Application Priority Data

Jul. 15, 1986 [JP] Japan ............ 61-166084
Jul. 22, 1986 [JP] Japan ............ 61-172626

[51] Int. Cl.[5] ............ C07K 3/22; C07K 3/20; C07K 3/28; C07K 15/06

[52] U.S. Cl. ............ 530/350; 435/215; 514/8; 514/21; 530/397; 530/399; 530/413; 530/416; 530/417; 530/834

[58] Field of Search ............ 424/85; 435/215; 514/8, 514/21; 530/359, 397, 399, 413, 417, 834, 416

[56] References Cited

U.S. PATENT DOCUMENTS

| | | | |
|---|---|---|---|
| 4,217,339 | 8/1980 | Bohn et al. | 530/392 X |
| 4,230,697 | 10/1980 | Nishida et al. | 530/834 X |
| 4,259,447 | 3/1981 | Hafeli | 435/215 |
| 4,286,063 | 8/1981 | Suyama | 435/215 |
| 4,301,064 | 11/1981 | Bohn | 530/834 X |
| 4,368,148 | 1/1983 | Bohn | 530/394 |
| 4,507,229 | 3/1985 | Bohn | 530/834 X |
| 4,594,328 | 6/1986 | Bohn et al. | 530/394 |
| 4,638,050 | 1/1987 | Aoki et al. | 530/413 |
| 4,677,195 | 6/1987 | Hewick et al. | 530/397 |
| 4,708,948 | 11/1987 | Iwata et al. | 424/85 X |
| 4,732,891 | 3/1988 | Maki et al. | 530/350 X |
| 4,736,018 | 4/1988 | Reutelingsperger | 530/391 |
| 4,748,156 | 5/1988 | Aoki et al. | 514/21 |

OTHER PUBLICATIONS

J. Clin. Invest. 76:2178–2181 (1985), Ishii et al.
Eur. J. Biochem. 151, 625–629 (1985), Reutelingsberger et al.
Arch. Gynak, 222, 5–13 (1977), Bohn et al.
J. Biochemistry, 102, 1261–1273 (1987), Iwasaki et al.

*Primary Examiner*—Howard E. Schain
*Attorney, Agent, or Firm*—Oblon, Spivak, McClelland, Maier & Neustadt

[57] ABSTRACT

Thrombin-binding substances are obtained by fractionating human urine by ion-exchange chromatography, affinity chromatography using a thrombin-bound carrier, immune adsorption column chromatography, gel filtration, and/or molecular-weight fractionation. One of the substances has a molecular weight of 46,500±6,000 in reduced condition and 39,000±10,000 in unreduced condition by SDS PAGE and an isoelectric point at pH 5.0–5.3, while the other has a molecular weight of 40,000±8,000 in reduced condition and 31,000±10,000 in unreduced condition by SDS PAGE and an isoelectric point at pH 4.9–5.7. They have strong affinity to thrombin. They are capable of promoting the thrombin catalyzed activation of protein C and prolong clotting time. They are stable to denaturing agents (urea and sodium dodecylsulfate).

8 Claims, No Drawings

THROMBIN-BINDING SUBSTANCE AND PROCESS FOR ITS PREPARATION

BACKGROUND OF THE INVENTION i) Field of the Invention

The present invention relates to a novel thrombin-binding substance, more particularly to a thrombin-binding substance useful as a medicine especially as a remedy for thrombosis and the like owing to its effects to the anticoagulation and fibrinolytic systems which control the coagulation of blood, and to a process for its preparation.

ii) Description of the Prior Art

A great deal of work has been done regarding the role that thrombin plays as a proteolytic enzyme in the control mechanism of blood coagulation and the mechanism of the coagulation system has been elucidated for the most part.

N. L. Esmon et al. have recently reported that thrombin activates in the organism Protein C which is said to act on the fibrinolytic and anticoagulant systems. They also reported the existence of a certain substance in extracts of rabbit lung tissue functioning as a coenzyme for the activation mechanism, and named it thrombomodulin [J. Biological Chemistry, 257(2) 859-864 (1982)].

Aoki, one of the present inventors, and others also reported human thrombomodulin separated from human placenta. The substance had similar properties to those reported by N. L. Esmon et al., with a molecular weight of about 71,000 in an unreduced condition [Thromb. Res. 37, 353-364 (1985)].

Furthermore, I. Maruyama et al. reported that they compared the activities of human thrombomodulin separated from human placentae and having a molecular weight of about 75,000 with those of the above rabbit thrombomodulin and they had identical activities [J. Clin, Invest. 75, 987-991, (March 1985)].

It has also been reported recently by H. Ishii et al. that human plasma and urine contain substances having the same activities as thrombomodulin and the molecular weights of such substances in plasma are about 63,000 and 54,000 [J. Clin. Invest. 76, 2178-2181 (Dec. 1985)].

SUMMARY OF THE INVENTION

The present inventors have been working extensively with a view toward developing an advantageous method for isolating and purifying the above human thrombomodulin. In the course of the research, two types of thrombin-binding substances different from the above human thrombomodulin have been found and separated from human urine. It has been found that these thrombin-binding substances are similar to each other and are novel compounds having lower molecular weights compared with the human thrombomodulin, leading to completion of this invention.

An object of this invention is therefore to provide a novel human thrombin-binding substance and a process for the preparation thereof.

In one aspect of this invention, there is thus provided a thrombin-binding substance derived from human urine and having the following characteristics:

(a) molecular weight:

46,500±6,000 in reduced condition by SDS PAGE
39,000±10,000 in unreduced condition by SDS PAGE (b) isoelectric point: pH 5.0-5.3

(c) affinity: strong affinity to thrombin (d) activity:

(1) capable of promoting the thrombin catalyzed activation of protein C (2) prolongs clotting time; and (e) stability: stable to denaturing agents (urea and sodium dodecylsulfate).

In another aspect of this invention, there is also provided a thrombin-binding substance derived from human urine and having the following characteristics:

(a) molecular weight:

40,000±8,000 in reduced condition by SDS PAGE
31,000±10,000 in unreduced condition by SDS PAGE (b) isoelectric point: pH 4.9-5.7

(c) affinity: strong affinity to thrombin (d) activity:

(1) capable of promoting the thrombin catalyzed activation of protein C (2) prolongs clotting time; and (e) stability: stable to denaturing agents (urea and sodium dodecylsulfate).

In a further aspect of this invention, there is also provided a process for preparing a thrombin-binding substance having the following characteristics:

(a) molecular weight:

46,500±6,000 in reduced condition by SDS PAGE
39,000±10,000 in unreduced condition by SDS PAGE (b) isoelectric point: pH 5.0-5.3

(c) affinity: strong affinity to thrombin (d) activity:

(1) capable of promoting the thrombin catalyzed activation of protein C (2) prolongs clotting time; and (e) stability: stable to denaturing agents (urea and sodium dodecylsulfate), which comprises fractionating human urine by ion-exchange chromatography, affinity chromatography using a thrombin-bound carrier, immune adsorption column chromatography, gel filtration, and/or molecular-weight fractionation.

In a still further aspect of this invention, there is also provided a process for preparing a thrombin-binding substance having the following characteristics:

(a) molecular weight:

40,000±8,000 in reduced condition by SDS PAGE
31,000±10,000 in unreduced condition by SDS PAGE (b) isoelectric point: pH 4.9-5.7

(c) affinity: strong affinity to thrombin (d) activity:

(1) capable of promoting the thrombin catalyzed activation of protein C (2) prolongs clotting time; and (e) stability: stable to denaturing agents (urea and sodium dodecylsulfate), which comprises fractionating human urine by ion-exchange chromatography, affinity chromatography using a thrombin-bound carrier, immune adsorption column chromatography, gel filtration, and/or molecular-weight fractionation.

The thrombin-binding substance of this invention is useful as a fibrinolytic accelerator or as an anticoagulant since it binds thrombin and specifically enhances the activation of protein C and prolongs the clotting time.

The above and other objects, features and advantages of the present invention will become apparent from the following description and the appended claims.

DETAILED DESCRIPTION OF THE INVENTION AND PREFERRED EMBODIMENTS

According to the present invention, the thrombin-binding substance can be prepared, for example, by fractionating fresh human urine or a human urine concentrate. The fractionation can be effected by suitably combining ion-exchange chromatography, affinity chromatography using a thrombin-bound carrier, immune adsorption column chromatography using a monoclonal antibody, gel filtration, molecular weight fractionation, etc. Among these methods, it is particularly preferred, for example, to conduct (1) ion-exchange chromatography, affinity chromatography, gel filtration and molecular weight fractionation successively or (2) immune adsorption column chromatography and ion-exchange chromatography successively.

The method (1) may be practised, for example, in the following manner. Benzamidine hydrochloride, aprotinin or the like is added to fresh urine. The resultant mixture is subjected to ion-exchange chromatography on "DEAE-Sephadex A-50" (trade name, product of Pharmacia AB), "DEAE-TOYOPEARL 650C", "DEAE-TOYOPEARL 650M", "DEAE-TOYOPEARL 650S" (trade names, products of Toyo Soda Mfg. Co., Ltd.), "QAE-Sephadex A-50" (trade name, product of Pharmacia AB), or the like to adsorb active fractions, followed by elution with a Tris-HCl buffer containing sodium chloride and benzamidine hydrochloride. After concentration of the active fraction, the concentrate is caused to pass through a column packed with a thrombin-bound carrier such as diisopropylphospho-thrombin-agarose so as to adsorb the active fraction. The active fraction is thereafter eluted with a Tris-HCl buffer which contains sodium chloride and benzamidine hydrochloride, thereby obtaining the active fraction.

The active fraction is concentrated further. Using "Sephadex G 150" (trade name, product of Pharmacia AB), "Ultrogel AcA34" (trade name, product of LKB Company) or the like, the resulting concentrate is subjected to gel filtration so as to collect the active fraction.

The substances of the present invention can then be obtained by subjecting the active fraction to molecular weight fractionation by an electrophoretic technique making use of a sodium dodecylsulfate (SDS)-polyacrylamide gel and collecting fractions having the molecular weights of the below-described thrombin-binding substances of this invention, for example, in accordance with the Laemmili's method [see, Nature, 227 680–685, (1970)].

The method (2) may be practised, for example, in the following manner. After dialyzing fresh urine against a buffer having a high salt concentration and approximately neutral pH, active fractions are collected by immune adsorption column chromatography. The active fractions are then subjected to high performance liquid chromatography on an ion-exchange resin, whereby fractions corresponding to the molecular weights of the thrombin-binding substances of this invention are collected to obtain the substances of this invention. As an immunoadsorbent useful for the immune adsorption column chromatography, may be mentioned a monoclonal antibody bound carrier in which a monoclonal antibody for the thrombin-binding substances is bound on an insoluble carrier such as dextran gel, agarose gel or polyvinyl gel. The monoclonal antibody for the thrombin-binding substances may be obtained, for example, by fusing mouse spleen cells, which have been immunized with the above-described thrombin-binding substance extracted from human placentae and having the molecular weight of about 71,000, with mouse myeloma cells P3-Ag8-$\gamma$ and then treating the resultant hybridomas in a manner known per se in the art. Of monoclonal antibodies available in the above-described manner, it is particularly preferred to use those capable of recognizing sites of the thrombin-binding substances which sites are not affected by calcium. The elution of the thrombin-binding substances from the immune adsorption column can be effected with a buffer containing potassium thiocyanate by way of example.

As a column useful in the practice of the high performance liquid chromatography, a column packed with an anion-exchange resin is preferred. "TSK gel DEAE-5PW", "TSK gel DEAE-2SW", "TSK gel DEAE-3SW" (trade names, products of Toyo Soda Mfg. Co., Ltd.), "Mono Q HR5/5" (trade name, product of Pharmacia AB), etc. may be mentioned by way of example.

The process of this invention is extremely efficient compared with the conventional placenta extraction process, since the process of this invention uses as a raw material human urine available in a large volume and the intended substance can be isolated and purified after separation of other useful substances such as urokinase.

The thus-obtained thrombin-binding substance of this invention is a mixture of two types of substances identified by (A) and (B), which have the following properties respectively:

(a) Molecular weight:

| | |
|---|---|
| (A) | 46,500 ± 6,000 in reduced condition |
| | 39,000 ± 10,000 in unreduced condition |
| (B) | 40,000 ± 8,000 in reduced condition |
| | 31,000 ± 10,000 in unreduced condition |

Measuring method:

Molecular weights were determined by an electrophoretic technique in accordance with the Laemmli's method (Nature, 227, 680–685, 1970), which used a 7.5% sodium dodecylsulfate(SDS)-polyacrylamide gel containing 5% urea. "Bio-Rad SDS-PAGE Standard for High-Molecular Substances" (trade name, product of Nippon Bio-Rad Laboratories Inc.) was used as a standard protein.

(b) Isoelectric point:

(A) pH 5.0–5.3

(B) pH 4.9–5.7

Ampholite was used to determine an isoelectric point for each fraction in electrophoresis.

(c) Affinity:

The substances of the present invention have strong affinity to thrombin. Nearly 100% of the substances of this invention were adsorbed in a chromatographic treatment using diisopropylphosphoro-(DIP)-thrombin-agarose [See, J. Biological Chemistry, 245, 3059–3065, (1970)].

(d) Activity:

(1) The substances of the present invention bind thrombin to activate protein C.

Measuring method:

Dissolved in 35 μl of a 0.02 M Tris-HCl buffer (PH 7.5) containing 0.1 M sodium chloride and 5 mM calcium chloride were 5 μl of 7.32 μM protein C, 10 μl of either one of the substances of this invention or human thrombomodulin extracted from placentae (0.5 μg/ml) and 50 μl of 5 U/ml thrombin. The solution was then incubated at 37° C. for 0–30 minutes, followed by an addition of 100 μl of 2 units/ml anti-thrombin III. The resulting mixture was incubated at 37° C. for 10 minutes, so that the reaction was terminated. To this solution, 200 μl of a buffer containing 0.02 mM Boc-Leu-Ser-Thr-Arg-MCA (product of Protein Research Foundation, Osaka, Japan) was added to effect a reaction at 37° C. for 10 minutes. Thereafter, 600 μl of 20% acetic acid was added to terminate the reaction. The concentration of the dissociated AMC was measured by a spectro-fluorometer at an exciting light wavelength of 380 nm and an emitting light wavelength of 460 nm, whereby the concentration of activated protein C was determined. Results are shown in Table 1.

TABLE 1

| Sample (0.5 μg/ml) | Concentration of AMC (μmol/ml · min × $10^{-3}$) |
|---|---|
| Invention (A) | 10 |
| substance (B) | 9 |
| Human thrombomodulin obtained from placentae | 6 |

(2) The substances of the present invention prolong the blood clotting time.

Measuring method:

Placed in a fibrocup were 100 μl of 1 U/ml cow thrombin (product of Mochida Pharmaceutical Co., Ltd.) and 100 μl of either one of the substances of this invention or human thrombomodulin extracted from placentae ($OD_{280}$: 0.5), and the contents were heated at 37° C. for 30 minutes. Then, 100 μl of 2 mg/ml human fibrinogen was added and a fibrometer manufactured by Becton-Dickinson Co. was turned on to measure the clotting time. The measurement was repeated twice. All samples were dissolved in 0.02 M imidazole-HCl buffer (pH 7.6) containing 0.15 M sodium chloride. The average of the resulting data is shown in Table 2.

TABLE 2

| Sample ($OD_{280}$: 0.5) | Clotting time (sec.) |
|---|---|
| Invention (A) | 154 |
| substance (B) | 144 |
| Human thrombomodulin | 120 |
| Control (not added) | 94 |

(e) Stability

| Conditions | Residual Activity (%) (A) | (B) |
|---|---|---|
| Reduction by 1% β-mercaptoethanol | 0 | 0 |
| Denaturing agent 1% SDS | 140 | 140 |
| Denaturing agent 8% urea | 170 | 140 |
| Denaturing agent 6M guanidium chloride | 70 | 60 |
| pH 2 | 25 | 40 |
| pH 10 | 90 | 100 |
| Pepsin treatment | 30 | 50 |
| Trypsin treatment | 80 | 80 |

The substances of this invention (0.045OD) were separately treated at 37° C. for 120 minutes under the conditions described above. After the treatments, the samples were separately diluted hundred-fold with a 0.02 M Tris-NaCl buffer to measure their activities. The residual activities were calculated respectively relative to the activity data of the substances before their treatments. The final concentrations of pepsin and trypsin were 2.5 μg/ml (pH 2.5) and 2.5 μg/ml (pH 7.5), respectively and the treatments were both conducted at 37° C. for eight hours.

Having generally described the invention, a more complete understanding can be obtained by reference to certain specific examples, which are provided herein for purposes of illustration only and are not intended to be limiting unless otherwise specified.

EXAMPLES

The present invention will hereinafter be described by the following Referential Example and Examples.

REFERENTIAL EXAMPLE (1) Production of monoclonal antibody:

The thrombin-binding substance (20 μg, molecular weight: 71,000) which had been extracted from human placentae and purified, was emulsified in the Freund's complete adjuvant and was then administered intraperitoneally to male BALB/c mice. The thrombin-binding substance was thereafter administered intraperitoneally in a dose of 20–100 μg at intervals of 2–4 weeks for 10 months, followed by a final intravenous administration of 100 μg.

Three days later, the spleens were taken out of the mice. Spleen cells were loosened in the Iscove's modified Dulbecco's medium (IMDM). Discrete cells which had passed through a 100-mesh screen were collected. After adding a hypotonic solution (155 mM ammonium chloride) to the cells to hemolyze erythrocytes, the cells were washed three times with IMDM.

Mouse myeloma cells (P3-Ag8-γ) were also washed three times with IMDM.

The numbers of both cells were counted. The spleen cells and P3-Ag8-γ were mixed at a ratio of 3:1, followed by centrifugation. The supernatant was discarded. After thoroughly disintegrating the precipitated cells, 1 ml 50% polyethylene glycol (1500) was added dropwise to effect their fusion. After allowing the cells to stand for 30 minutes at room temperature, the cells were gently stirred while dropping 1 ml IMDM over 1 minutes and then 10 ml IMDM in the course of 5 minutes. The volume of the mixture reached 50 m; finally, followed by centrifugation at 1,000 rpm for 8 minutes. The precipitate was suspended in IMDM added with 10% FCS. Centrifugation was conducted again and the supernatant was discarded. The resultant cells were again suspended at $3\times10^5$/ml in HAT-containing IMDM with 10% FCS added therein. The resulting suspension was poured 100μl by 100μl into the individual wells of a 96-well microplate. The culture medium was added in an amount of 50 μl with intervals of 3–4 days. Owing to the selection of the above culture medium, hybridomas alone were allowed to grow.

Culture broths were collected separately from wells in which hybridomas had grown. Wells with the intended antibody produced therein were then determined by an enzyme immunoassay.

Peritoneal cells ($1\times10^5$/ml;), which had been collected by injecting IMDM into the abdominal cavities of normal mice, were suspended in IMDM added with 10% FCS and the resultant suspension were poured 100 μl by 100 μl into the individual wells of a 96-well microplate. On the following day, the antibody-producing hybridomas were diluted to 5 cells/ml and added in an amount of 100 μl per well into the wells. The culture medium was either added or replaced on the every third day. Supernatant was collected from each well in which cells had grown and the production of the antibody was confirmed by the enzyme immunoassay. Positive wells were subjected again to cloning so that cloned hybridomas TM-H54, TM-H59, TM-H60, TM-H65, TM-H73 and TM-H91, which were able to produce monoclonal antibodies, were obtained.

BALB/c mice of at least 7 weeks of age were intraperitoneally administered with 0.5 m; pristane. About one week later, the above-described hybridoma TM-H59 was inoculated intraperitoneally at a rate of $1\times10^6$ cells/mouse. Ten days later, ascites was collected from the mice and centrifuged at 3,000 rpm for 10 minutes, and the supernatant was separated. Added to 4.8 m; of this supernatant was the same volume of a 1.5 M glycine buffer (pH 8.9) containing 3 M sodium chloride. The resultant mixture was caused to pass through a column of 5 ml Protein A Sepharose CL-4B which had been equilibrated with the same buffer. After washing the column thoroughly with the buffer, the column was eluted with a 0.1 M citrate buffer (pH 4.0). The eluate was collected 3 ml by 3 ml in test tubes each of which contained 1 ml 1 M Tris-HCl buffer (pH 8.0). Their $A_{280}$ values were measured to collect protein fractions. After dialyzing the protein fractions against water, they were lyophilized to obtain 60 mg of a monoclonal antibody. The thus-obtained monoclonal antibody (TM-A59) had the following characteristics:

Molecular weight: 190,000±5,000

IgG subclass: IgGl

Isoelectric point: 7.1–7.6

(2) Production of an immunoadsorbent:

After washing 3 g of BrCN-activated Sepharose 4B successively with 1 mM hydrochloric acid and 0.1 M sodium carbonate buffer (pH 8.3) containing 0.1 M sodium chloride, it was converted into an 8-ml liquid mixture in the above buffer. To the liquid mixture, 20 mg of the monoclonal antibody (TM-A59) obtained in the above procedure (1) was added. The resultant mixture was shaken at room temperature for 2 hours, followed by removal of water through a glass filter. In addition, 40 ml of 1 M Tris-HCl buffer (pH 8.0) was added and the thus-obtained mixture was shaken for 2 hours, and added 40 ml of 0.1 M acetate buffer (pH 4.0). The obtained mixture was shaken for 2 hours followed by removal of water through a glass filter. The thus-obtained antibody-bound Sepharose was washed three times alternately with 0.1 M Tris-HCl buffer (pH 8.3) containing 0.5 M sodium chloride and 0.1 M acetate buffer (pH 4.0) containing 0.5 M sodium chloride. It was then equilibrated with 0.02 M Tris-HCl buffer (pH 7.6) containing 1 M sodium chloride and 0.05% Lubrol to obtain an immunoadsorbent.

EXAMPLE 1

(1) A solution of 10 l fresh human urine with 10 ml of 1 M benzamidine hydrochloride and 5 ml of aprotinin added therein was adjusted at 4° C. to pH 8–11 with 6N sodium hydroxide. After allowing the resultant solution to stand overnight, the resulting precipitate was removed. Added to the thus-obtained supernatant was 1 l of "QAE-Sephadex A-50" which had been equilibrated with 0.02 M 3-(cyclohexylamino)-1-propane-sulfonic acid (pH 10.5) in advance, followed by overnight stirring. The supernatant was removed and the resin was washed with 1 l of 0.02 M 3-(cyclohexyl-amino)-1-propanesulfonic acid (pH 10.5), followed by further washing with 2 l of a physiological saline added with Tris-HCl buffer (TBS, pH 7.6). Thereafter, the resin was eluted with 3 l TBS (pH 7.6) which contained 1 M sodium chloride. The resulting eluate was dialyzed three times using 10 ; TBS (pH 7.6) as an external dialyzing solution. Three liters of the thus-dialyzed solution were then subjected to column chromatography on "DEAE-Sephadex A-50" which had been equilibrated by the above buffer. The column (φ3.7 cm×2.5 cm) was eluted in accordance with the gradient technique, using 0.1–1 M sodium chloride in 0.02 M Tris-HCl buffer which contained 1 mM benzamidine hydrochloride. The eluate was fractionated into 20 ml portions and active fractions were collected.

The optical absorbance and relative activity of the active fraction were $A_{280=0.170}$ (400 ml) and 137 units/$OD_{280}$, respectively.

(2) The active fraction (400 ml) was subjected to a DIP-thrombin-agarose column (2.5 cm across×20 cm long) which had been equilibrated with the same buffer as that used for the extraction. The column was then washed with 500 ml of the same buffer.

The column was then eluted at a gradient concentration of 0.1 M–1 M sodium chloride in a 0.02 M Tris-HCl buffer (pH 7.5) containing 1 mM benzamidine hydrochloride, so that active fractions (Nos. 20–65) were collected.

The optical absorbance and relative activity of the active fractions were $A_{280}$=0.111 (600 ml) and 235 units/$OD_{280}$, respectively.

(3) The active fractions (600 ml) were concentrated to about 10 ml using "Millipore CX-10" (trade name, product of Millipore Corporation) and then charged into a column, 2.7 cm across×150 cm long, of "ACA 34" (trade name, product of LKB Co.) which had been equilibrated with a 0.02 M Tris-HCl buffer (pH 7.5) containing 0.1 M NaCl and 1 mM benzamidine hydrochloride. The column was eluted with the above buffer to collect active fractions (Nos. 115–140).

The optical absorbance and relative activity of the active fractions were $A_{280}$=1.8 (1.6 ml) and 1,100 units/$OD_{280}$, respectively. (4) Using Millipore CX-10, 1.6 ml of the active fractions thus obtained was concentrated to about 500 μl, to which a solution of 500 μl 20% SDS and 100 μl 50% glycerol were added. The active fractions were then subjected to electrophoresis using 10% SDS-polyacrylamide gel in accordance with the Laemmli's method [see, Nature, 227, 680–685 (1970)]. Portions containing the active fractions were then cut off and immersed in a 0.02 M phosphate buffer (pH 7.5) containing 0.1% Tween 80 and 0.1 M sodium chloride, in which the portions were eluted at 4° C. for 24 hours. The eluate was concentrated to about 100 82 l using Millipore CX-10. The intended substance (A) having a protein concentration of 230 μg/ml was obtained. Example 2:

Fresh human urine (1 l) was dialyzed overnight against a 0.02 M Tris-HCl buffer (pH 7.6) which contained 1 M sodium chloride and 0.1% Lubrol. The thus-dialyzed solution was adsorbed on 10 ml the immunoadsorbent obtained in accordance with the Referential Example and packed in a column. After washing the column with the above buffer, the column was eluted with a Tris-HCl buffer (pH 7.6) which contained 2 M potassium thiocyanate and 0.1% Lubrol. The eluate was fractionated into 5 ml portions. Active fractions (Fraction Nos. 2-15) were combined together, followed by concentration to 3 ml with Millipore CX-10.

The above concentrate was subjected to high performance liquid chromatography on DEAE-5PW, followed by elution in accordance with the gradient technique, using 0.02 M Tris-HCl buffer (pH 7.6) which contained 0-1 M sodium chloride and 0.1% Lubrol. The eluate was fractionated into 1 ml portions.

Fraction Nos. 23-27 were combined together and concentrated to about 100 μl using Millipore CX-10, whereby the intended substance (A) having a protein concentration of 20 μg/ml was obtained.

Fraction Nos. 15-19 were also combined together, followed by concentration to about 100 μl with Millipore CX-10 to obtain the intended substance (B) having a protein concentration of 15 μg/ml.

Having now fully described the invention, it will be apparent to one of ordinary skill in the art that many changes and modifications can be made thereto without departing from the spirit or scope of the invention as set forth herein.

We claim:

1. A thrombin binding substance prepared by a process comprising:

successively subjecting human urine to ion exchange chromatography, affinity chromatography employing a column with a thrombin-bound carrier, gel filtration, and molecular weight fractionation, said thrombin-binding substance having the following characteristics:

(a) molecular weight:
46,500±6,000 in reduced condition by SDS PAGE
39,000±10,000 in unreduced condition by SDS PAGE (b) isoelectric point: pH 5.0-5.3

(c) affinity: strong affinity to thrombin (d) activity:
(1) capable of promoting the thrombin catalyzed activation of protein C
(2) prolongs clotting time; and (e) stability; stable to denaturing agents (urea an sodium dodecylsulfate).

2. A thrombin-binding substance prepared by a process comprising:

successively subjecting human urine to ion exchange chromatography, affinity chromatography employing a column packed with a thrombin-bound carrier gel filtration and molecular weight fractionation, said thrombin-binding substance having the following characteristics:

(a) molecular weight:
40,000±8,000 in reduced condition by SDS PAGE; 31,000±10,000 in unreduced condition by SDS PAGE (b) isoelectric point: pH 4.9-5.7

(c) affinity: strong affinity to thrombin (d) activity:
(1) capable of promoting the thrombin catalyzed activation of protein C
(2) prolongs clotting time; and (e) stability: stable to denaturing agents (urea and sodium dodecylsulfate).

3. The thrombin-binding substance of claim 1, wherein prior to ion exchange chromatography, benzamidene hydrochloride or aprotinin is added to said urine.

4. The thrombin-binding substance of claim 2, wherein prior to ion exchange chromatography, benzamidene hydrochloride or aprotinin is added to said urine.

5. A thrombin-binding substance prepared by a process, comprising:

subjecting human urine to immune adsorption column chromatography which uses a packing having a monoclonal antibody specific to a thrombin-binding substance bound on an insoluble carrier followed by ion exchange chromatography, said thrombin-binding substance having the following characteristics:

(a) molecular weight
46,500±6,000 in reduced condition by SDS PAGE;
39,000±10,000 in unreduced condition by SDS PAGE (b) isoelectric point: pH 5.0-5.3

(c) affinity: strong affinity to thrombin (d) activity:
(1) capable of promoting the thrombin catalyzed activation of protein C
(2) prolongs clotting time; and (e) stability: stable to denaturing agents (urea and sodium dodecylsulfate).

6. A thrombin-binding substance prepared by a process comprising:

subjecting human urine to immune adsorption column chromatography which uses a packing having a monoclonal antibody specific to said thrombin-binding substance bound on an insoluble carrier followed by ion exchange chromatography, said thrombin-binding substance having the following characteristics:

(a) molecular weight:
40,000±8,000 in reduced condition by SDS PAGE; 31,000±10,000 in unreduced condition by SDS PAGE (b) isoelectric point: pH 4.9-5.7

(c) affinity: strong affinity to thrombin (d) activity:
(1) capable of promoting the thrombin catalyzed activation of protein C
(2) prolongs clotting time; and (e) stability: stable to denaturing agents (urea and sodium dodecylsulfate).

7. A thrombin-binding substance prepared by a process comprising:

adding benzamidine hydrochloride and/or aprotinin to human urine, and then successively subjecting said treated urine to ion-exchange chromatography, affinity chromatography employing a column packed with a thrombin-bound carrier, gel filtration and molecular weight fractionation, said thrombin-binding substance having the following characteristics:

(a) molecular weight:

40,000±8,000 in reduced condition by SDS PAGE; 31,000±10,000 in unreduced condition by SDS PAGE (b) isoelectric point: pH 4.9–5.7

(c) affinity: strong affinity to thrombin (d) activity:

(1) capable of promoting the thrombin catalyzed activation of protein C (2) prolongs clotting time; and (e) stability: stable to denaturing agents (urea and sodium dodecylsulfate).

8. A thrombin-binding substance prepared by a process comprising:

adding benzamidine hydrochloride and/or aprotinin to human urine, and then successively subjecting said treated urine to ion-exchange chromatography, affinity chromatography employing a column packed with a thrombin-bound carrier, gel filtration and molecular weight fractionation, said thrombin-binding substance having the following characteristics:

(a) molecular weight:

46,500±6,000 in reduced condition by SDS PAGE; 39,000±10,000 in unreduced condition by SDS PAGE (b) isoelectric point: pH 5.0–5.3

(c) affinity: strong affinity to thrombin (d) activity:

(1) capable of promoting the thrombin catalyzed activation of protein C (2) prolongs clotting time; and (e) stability: stable to denaturing agents (urea and sodium dodecylsulfate).

* * * * *